United States Patent [19]

Robertson et al.

[11] Patent Number: 4,876,282

[45] Date of Patent: Oct. 24, 1989

[54] 1-PHENYLALKYLAMINES AS SELECTIVE SEROTONIN UPTAKE INHIBITORS

[75] Inventors: David W. Robertson, Greenwood; David T. Wong, Indianapolis, both of Ind.

[73] Assignee: Eli Lilly and Company, Indianapolis, Ind.

[21] Appl. No.: 125,110

[22] Filed: Nov. 25, 1987

[51] Int. Cl.$^4$ ............................................ A61K 31/207
[52] U.S. Cl. .................................. 514/554; 514/555; 514/649; 514/811; 514/813; 564/304; 564/373; 562/597
[58] Field of Search ............... 564/315, 316, 373, 378, 564/387; 260/501.1, 501.18; 514/648, 649, 656, 554, 555, 811, 813

[56] References Cited

U.S. PATENT DOCUMENTS

| | | | |
|---|---|---|---|
| 3,079,403 | 2/1963 | Weinstock | 564/347 X |
| 3,138,639 | 6/1964 | Brossi et al. | 564/373 |
| 3,178,477 | 4/1965 | Seeger et al. | 564/373 |
| 3,308,157 | 3/1967 | Robertson et al. | 564/378 X |
| 3,689,504 | 9/1972 | Horrom | 564/378 X |
| 3,814,750 | 6/1974 | Cross et al. | 260/239 B |
| 3,972,935 | 8/1976 | Molloy | 564/316 |
| 4,018,895 | 4/1977 | Molloy et al. | 424/330 |
| 4,034,011 | 7/1977 | Molloy | 564/316 |
| 4,062,955 | 12/1977 | Burn et al. | 564/387 X |
| 4,194,009 | 3/1980 | Molloy et al. | 424/330 |
| 4,207,343 | 6/1980 | Lavagnino et al. | 424/330 |
| 4,314,081 | 2/1982 | Molloy et al. | 564/347 |
| 4,329,356 | 5/1982 | Holland | 424/274 |

FOREIGN PATENT DOCUMENTS 2060618 5/1981 United Kingdom.

OTHER PUBLICATIONS

Clark et al., *Journal of Medicinal Chemistry*, vol. 22, No. 11, 1373–1379 (1979).

*Primary Examiner*—Robert V. Hines
*Attorney, Agent, or Firm*—Robert A. Conrad; Leroy Whitaker

[57] ABSTRACT

The present invention provides 1-phenyl-(naphthalenyl)alkylamines which are selective inhibitors of serotonin uptake.

19 Claims, No Drawings

1-PHENYLALKYLAMINES AS SELECTIVE SEROTONIN UPTAKE INHIBITORS

BACKGROUND OF THE INVENTION

The relationship between monoamine uptake and a variety of diseases and conditions continues to be investigated in an effort to find compounds with both improved efficacy and selectivity so as to eliminate unwanted side effects. One such monoamine, serotonin (5-hydroxytryptamine), has been studied extensively because of its known association with a variety of mammalian disorders. A number of compounds have been shown to have an effect on serotonin. For example, the hydrochloride salt of fluoxetine (dl-N-methyl-3-phenyl-3-[4-(trifluoromethyl)phenoxy]propanamine) is a selective serotonin uptake inhibitor presently undergoing clinical evaluation for the treatment of depression, eating disorders, alcoholism, and other disorders. Similarly, tomoxetine hydrochloride ((−)-N-methyl-3-phenyl-3-(2-methylphenoxy)propanamine hydrochloride) is a selective inhibitor of norepinephrine uptake being investigated clinically for its antidepressant activity. These compounds are among many taught in U.S. Pat. Nos. 4,018,895, 4,194,009, and 4,314,081 as being potent blockers of the uptake of various physiologically active monoamines including serotonin, norepinephrine and dopamine.

U.S. Pat. No. 4,207,343 discloses 1-phenyl-3-(substituted phenoxy)propanamines again having the ability to block a variety of monoamines.

SUMMARY OF THE INVENTION

The present invention provides novel 1-phenylalkylamines which are selective inhibitors of serotonin uptake, and would therefore be expected to produce fewer side effects following administration since the compounds do not effectively block other monoamines such as norepinephrine. More specifically, the present invention relates to a compound of the formula

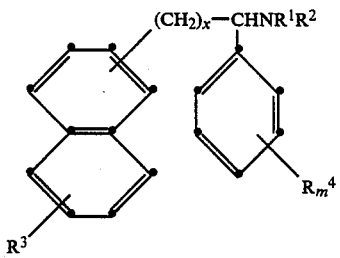

wherein:
each of $R^1$ and $R^2$ independently is hydrogen or methyl;
$R^3$ is hydrogen, halo, $C_1$-$C_4$ alkyl, $C_1$-$C_3$ alkoxy or trifluoromethyl;
each $R^4$ independently is hydrogen, halo, $C_1$-$C_4$ alkyl, $C_1$-$C_3$ alkoxy or trifluoromethyl;
m is 1 or 2;
when m is 2, each $R^4$ can be combined to form methylenedioxy;
x is 2–5; or
a pharmaceutically acceptable acid addition salt thereof.

The invention also provides pharmaceutical formulations comprising a compound of the above formula and a pharmaceutically acceptable carrier, diluent or excipient therefor.

Further embodiments of the invention are methods for selectively inhibiting the uptake of serotonin, as well as methods for treating a variety of disorders which have been linked to decreased neurotransmission of serotonin in mammals including obesity, depression, alcoholism, pain, loss of memory, anxiety, smoking, and the like, employing a compound of the invention.

DETAILED DESCRIPTION OF THE INVENTION

In the above formula, the term $C_1$-$C_4$ alkyl represents a straight or branched alkyl chain bearing from one to four carbon atoms. Typical $C_1$-$C_4$ alkyl groups include methyl, ethyl, n-propyl, isopropyl, n-butyl, isobutyl, sec.-butyl and t-butyl.

$C_1$-$C_3$ Alkoxy represents methoxy, ethoxy, n-propoxy or isopropoxy.

Halo represents fluoro, chloro, bromo or iodo.

The naphthalenyl substituent can be either 1-naphthalenyl or 2-naphthalenyl.

While all of the compounds of the present invention are believed to inhibit the uptake of serotonin in mammals, there are certain of these compounds which are preferred for such uses. Preferably one of $R^1$ and $R^2$ is hydrogen and the other is methyl. Especially preferred compounds are those wherein both $R^1$ and $R^2$ are methyl and x is 3. Other preferred aspects of the present invention will be noted hereinafter.

The compounds of the present invention possess an asymmetric carbon represented by the carbon atom labeled "C" in the following formula:

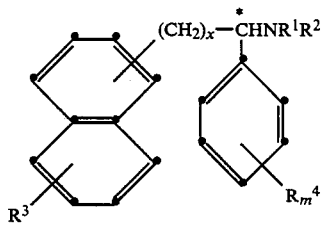

As such, the compounds can exist as the individual stereoisomers, as well as the racemic mixture of such isomers. Accordingly, the compounds of the present invention will include not only the d,l-racemates, but also their respective optically active d- and l-isomers.

As pointed out above, this invention includes the pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature or solids with low melting points, it is preferable to convert the free amines to their corresponding pharmaceutically acceptable acid addition salts, which are routinely solid at room temperature, for ease of handling. Further, since salts of the compounds of the present invention are typically more water soluble than their corresponding free amines, these salts may be preferred in an effort to increase bioavailability of the active agent following administration. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such oxalic acid and maleic acid.

The following compounds further illustrate compounds contemplated within the scope of the present invention:

N-Methyl-1-phenyl-3-(1-naphthalenyl)propylaminium phosphate (+)-N-Methyl-1-(4-methylphenyl)-4-(2-naphthalenyl)-butylaminium citrate N,N-Dimethyl-1-(3-bromophenyl)-4-(4-chloro-1-naphthalenyl)butylaminium hydrochloride (−)-N-Methyl-1-(3-chlorophenyl)-3-(5-methyl-2-naphthalenyl)propylaminium hydrobromide (+)-N-Methyl-1-(2-ethylphenyl)-5-[3-(trifluoromethyl)-1-naphthalenyl]pentylaminium oxalate N-Methyl-1-(4-fluorophenyl)-3-(6-iodo-1-naphthalenyl)propylaminium maleate (+)-N,N-Dimethyl-1-(3-methoxyphenyl)-4-(1-naphthalenyl)butylaminium formate N,N-Dimethyl-1-(4-n-propylphenyl)-4-(2-naphthalenyl)butylamine (−)-N-Methyl-1-[3-(trifluoromethyl)phenyl]-(1-naphthalenyl)pentylaminium sulfate N-Methyl-1-(4-methylphenyl)-3-(4-methyl-1-naphthalenyl)propylaminium oxalate (−)-N-Methyl-1-(2-bromophenyl)-4-(2-naphthalenyl)-butylaminium hydrochloride N,N-Dimethyl-1-(4-ethoxy-3-chlorophenyl)-4(6-iodo-2-naphthalenyl)butylaminium malonate N,N-Dimethyl-1-(2-ethylphenyl)-4-(1-naphthalenyl)-butylaminium hydroiodide N,N-Dimethyl-1-(3,4-difluorophenyl)-3-(4-methyl-2-naphthalenyl)propylaminium maleate (+)-N-Methyl-1-(4-chlorophenyl)-4-(2-naphthalenyl)-butylaminium caprate N-Methyl-1-(2-methoxyphenyl)-4-(6-n-propyl-1-naphthalenyl)butylaminium citrate (−)-N,N-Dimethyl-1-(3-ethylphenyl)-5-(2-methyl-1-naphthalenyl)pentylaminium monohydrogen phosphate 1-(4-Bromophenyl)-3-(1-naphthalenyl)propylaminium succinate (+)-1-(3,4-Dimethylphenyl)-4-[3-(trifluoromethyl)-1-naphthalenyl]butylaminium acetate N-Methyl-1-(4-methoxyphenyl)-4-(6-methyl-1-naphthalenyl)butylaminium tartrate (+)-1-(2-Iodophenyl)-5-(2-naphthalenyl)pentylaminium N-Methyl-1-(3-methylphenyl)-3-(4-n-butyl-1-naphthalenyl)propylaminium methanesulfonate (+)-1-(4-Chlorophenyl)-4-(2-chloro-1-naphthalenyl)-butylaminium oxalate (−)-N-Methyl-1-phenyl-4-(1-naphthalenyl)-butylaminium tartrate The compounds of the present invention may be prepared by procedures well known to those of ordinary skill in the art. The compounds are preferably synthesized by reacting a naphthalenylalkylhalide derivative with a phenylacetic acid dianion to provide the corresponding 1-phenyl(naphthalenyl)alkylcarboxylic acid. This compound is converted to the corresponding 1-isocyano-1-phenyl(naphthalenyl)alkane which is hydrolyzed to the corresponding 1-phenyl(nphthalenyl)alkylamine of the invention. This compound may then be converted to the N-methyl or N,N-dimethyl analog, if desired. The scheme for this reaction is represented by the following:

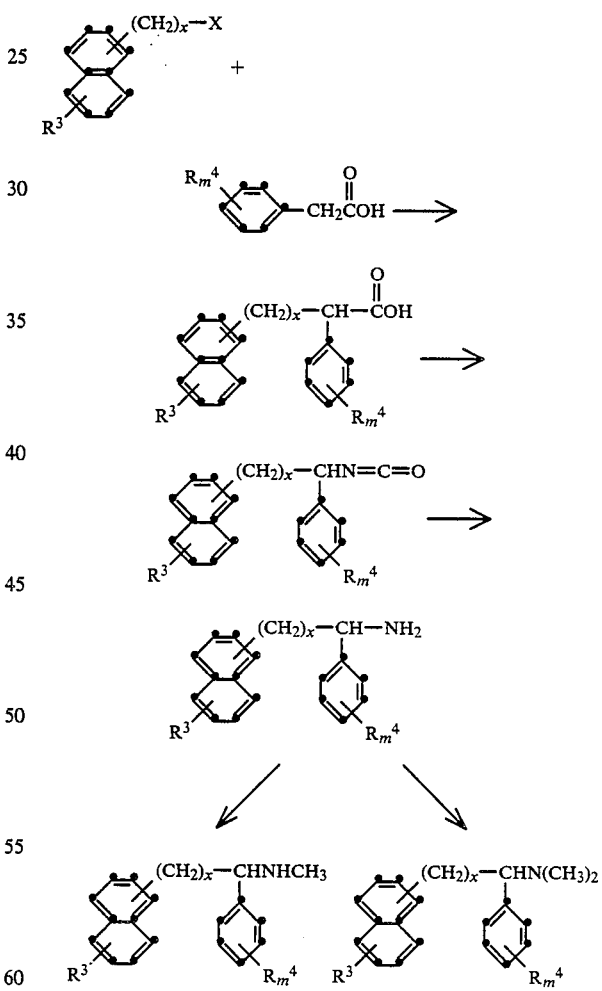

wherein $R^3$, $R^4$, m and x are as defined above and X is halogen.

According to the first step of the reaction, a phenylacetic acid derivative is dissolved in a mutual solvent under anhydrous conditions. To this mixture is added an alkyl alkali metal reagent and a suitable condensing agent. Typical solvents suitable for use in this reaction are preferably dried and include the aprotic solvents such as the ethers, for example diethyl ether, and the cyclic ethers, such as tetrahydrofuran, which is preferred. Exemplary alkyl alkali metal reagents include sec.-butyllithium and n-butyllithium, which is preferred. A typical and preferred condensing agent is hexamethylphosphoramide (HMPA). The reaction is typically cooled to a temperature in the range of about −100° C. to about −25° C., more preferably at a temperature in the range of about −80° C. to about −70° C., and a dilute solution of an equimolar quantity of the naphthalenylalkyl halide is added dropwise to the mixture. The mixture is allowed to stir for approximately 8 to 24 hours and is diluted with water. The desired product is isolated by acidifying the mixture with a suitable acid and extracting the mixture with a suitable water immiscible organic solvent such as diethyl ether. The solvent is removed, preferably by evaporation under vacuum, and the resulting product is further purified, if desired, by standard techniques such as purification over solid supports, such as silica gel or alumina, or crystallization from common solvents.

In the second step of the above described process, the 1-phenyl(naphthalenyl)alkylcarboxylic acid thus synthesized is converted to the corresponding 1-isocyano-1-phenyl(naphthalenyl)alkane. This reaction was conducted by dissolving the carboxylic acid derivative in a suitable solvent and cooling the resulting mixture to about 0° C. To this mixture a suitable base such as triethylamine is added followed by the dropwise addition of ethyl chloroformate. To this mixture is added dropwise approximately equimolar quantities of sodium azide dissolved in a small amount of water. The reaction is substantially completed after about 30 minutes to about 12 hours when conducted at a temperature in the range of about 0° C. to about 20° C. The reaction mixture is extracted with a suitable water immisible solvent and the resulting organic solution containing the product is purified according to standard procedures. The resulting acylazide intermediate is combined with an inert solvent, such as toluene, and stirred at a temperature in the range of about 25° C. to about 110° C. to provide the desired isocyano compound.

The compounds of the invention wherein $R^1$ and $R^2$ are both hydrogen are finally synthesized by hydrolyzing the 1-isocyano compound with a suitable acid. Typical acids include the hydrohalic acids such as hydrochloric acid. The reaction is substantially complete after about 1 hour to about 24 hours when conducted at a temperature in the range of about 20° C. to about 100° C. The desired product is isolated by raising the pH of the reaction mixture to approximately 8, and either isolating the desired compound by extraction by a suitable water immiscible solvent or collecting the precipitated product by vacuum filtration. The product thus synthesized can be further purified if desired by standard procedures.

Compounds of the present invention wherein $R^1$ and $R^2$ are both methyl are synthesized by reacting the primary amine compound of the invention with an excess of formaldehyde in the presence of sodium cyanoborohydride and a mutual solvent.

Compounds of the present invention wherein one of $R^1$ and $R^2$ is methyl and the other is hydrogen are preferably prepared by reacting the primary amine with ethyl chloroformate in the presence of triethylamine and a suitable solvent to provide the corresponding carbamate intermediate, which is then reduced in the presence of a suitable reducing agent such a lithium aluminum hydride to provide the N-methyl compounds of the present invention.

The compounds of the present invention wherein one of $R^1$ and $R^2$ is hydrogen and the other is methyl may also be prepared by demethylating the corresponding N,N-dimethylpropanamine. Preferably, a reagent such a phenyl chloroformate or trichloroethyl chloroformate is reacted with the N,N-dimethylpropanamine to provide the corresponding intermediate, which is then hydrolyzed to provide the corresponding N-methylpropanamine.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and the Like.

The compounds employed as starting materials in the synthesis of the compounds of the invention are well known and readily synthesized by standard procedures commonly employed by those of ordinary skill in the art.

The pharmaceutically acceptable acid addition salts of the invention are typically formed by reacting a 1-phenyl(naphthalenyl)alkylamine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

1-Phenyl-4-(1-napthalenyl)butylaminium oxalate

A. 5-(1-Naphthalenyl)-2-phenylpentanoic acid n-Butyllithium (89.7 ml of a 1.48 M solution in hexane; 132.7 mmol) was added dropwise to a solution of phenylacetic acid (8.81 g, 64.7 mmol) and HMPA (11.26 ml, 64.7 mmol) in 250 ml of THF at 0° C. The reaction mixture was stirred at room temperature for one hour and cooled to about −78° C. A solution of 3-(1-naphthalenyl)-propylbromide was added dropwise, and the resulting mixture was stirred at room temperature overnight. The mixture was diluted with water and washed twice with diethyl ether. The aqueous layer was acidified with concentrated hydrochloric acid and extracted three times with diethyl ether. The organic extracts were combined, washed with water and brine, dried over anhydrous sodium sulfate and concentrated in vacuo to afford 19.67 g of residue. Crystallization of the residue from diethyl ether/hexane provided 14.77 g of 5-(1-naphthalenyl)-2-phenylpentanoic acid. Yield 75%. mp=99°–100° C.

Analysis calculated for $C_{21}H_{20}O_2$ Theory: C, 82.86; H, 6.62; Found: C, 82.67; H, 6.58.

B. 1-Phenyl-4-(1-naphthalenyl)isocyanate

Ethyl chloroformate (4.7 ml, 49.2 mmol) was added dropwise to a solution of 5-(1-naphthalenyl)-2-phenylpentanoic acid (14.37 g, 47.3 mmol) and triethylamine (6.85 ml, 49.2 mmol) in 400 ml of acetone at about 0° C. A white precipitate formed, and the mixture was stirred for 30 minutes at about 0° C. A solution of sodium azide (5.84 g, 89.8 mmol) in water was added, and the mixture was stirred for an additional one hour at about 0° C. The mixture was diluted with water and extracted with toluene. The organic layer was washed with water and brine, dried over anhydrous sodium sulfate, heated on a steam bath for about 2.5 hours, and concentrated in vacuo to afford 12.33 g of 1-phenyl-4-(1-naphthalenyl)isocyanate as an oil.

C. Two hundred milliliters of 8N hydrochloric acid were added to a solution of 1-phenyl-4-(1-naphthalenyl)isocyanate in 400 ml of dioxane, and the mixture was stirred for about 2.5 hours at room temperature. The volatile constituents were removed under vacuum. The residue was basified with 5N sodium hydroxide, and the mixture was extracted with diethyl ether. The organic phase was washed with water and brine, dried over anhydrous sodium sulfate, and concentrated under vacuum to provide 12.0 g of an oil. The oil was flash chromatographed over silica gel using 0–8% methanol in methylene chloride (v:v) as the gradient to provide 8.62 g of 1-phenyl-4-(1-naphthalenyl)butylamine as an oil. A small portion of the oil was combined with oxalic acid and recrystallized from ethyl acetate/methanol to afford 1-phenyl-4-(1-naphthalenyl)butylaminium oxalate as a white solid. mp = 167°–168° C.

Analysis calculated for $C_{22}H_{23}NO_4$ Theory: C, 72.31; H, 6.34; N, 3.83; Found: C, 72.51; H, 6.24; N, 4.09.

EXAMPLE 2

N,N-Dimethyl-1-phenyl-4-(1-naphthalenyl)butylaminium oxalate

A 37% aqueous solution of formaldehyde (2.97 ml, 37.1 mmol) was added to a solution of 1-phenyl-4-(1-naphthalenyl)butylamine (2.04 g, 7.4 mmol) in 100 ml of acetonitrile. After twenty minutes, sodium cyanoborohydride (746 mg, 11.9 mmol) was added and the mixture was stirred for approximately 4.5 hours at room temperature. Glacial acetic acid was added periodically to maintain a neutral reaction pH. The mixture was diluted with water, basified with 5N sodium hydroxide, and extracted with diethyl ether. The ether layer was washed with water and brine, dried over anhydrous sodium sulfate and concentrated in vacuo to provide 2.28 g of an oil. The oxalate salt of the oil was prepared and purified employing preparative HPLC and recrystallization from ethyl acetate/methanol to provide 830 mg of N,N-dimethyl-1-phenyl-4-(1-naphthalenyl)butylaminium oxalate as a white solid. Yield 28.5%. mp = 122°–123° C.

Analysis calculated for $C_{24}H_{27}NO_4$ Theory: C, 73.26; H, 6.92; N, 3.56; Found: C, 73.00; H, 7.12; N, 3.32.

EXAMPLE 3

N-Methyl-1-phenyl-4-(1-naphthalenyl)butyl-aminium oxalate

Ethyl chloroformate (1.4 ml, 14.4 mmol) was added dropwise to a solution of triethylamine (2.0 ml, 14.4 mmol) and 1-phenyl-4-(1-naphthalenyl)butylamine (3.59 g, 13.1 mmol) in 100 ml of THF, and the mixture was stirred at room temperature for 2 hours. The solvent was removed in vacuo, water was added, and the mixture was extracted with ether. The organic layer was washed with water, 1N hydrochloric acid, water, 1N sodium hydroxide, water and brine, dried over anhydrous sodium sulfate and concentrated in vacuo to afford 4.71 g of residue.

A solution of the residue prepared above in 100 ml of THF was added dropwise to a mixture of lithium aluminum hydride (3.47 g, 91.4 mmol) in 50 ml of THF. The reaction mixture was warmed to about 55° C. for 6 hours, cooled to 0° C., and then quenched by the dropwise addition of a saturated sodium sulfate solution. The precipitate was removed by filtration. The filtrate was concentrated under vacuum and the residue was purified by flash chromatography over silica gel using 0–10% methanol in methylene chloride (v:v) as the gradient. The oxalate salt was prepared and crystallized from ethyl acetate/methanol to afford 2.35 g of N-methyl-1-phenyl-4-(1-naphthalenyl)butylaminium oxalate as a white solid. Yield 47.5%. mp = 173°–175.5° C.

Analysis calculated for $C_{23}H_{25}NO_4$ Theory: C, 72.80; H, 6.64; N, 3.69; Found: C, 72.64; H, 6.56; N, 3.76.

The following compound was prepared according to the general procedures outlined above.

EXAMPLE 4

N,N-Dimethyl-1-phenyl-3-(1-naphthalenyl)propylaminium oxalate, m.p. = 142°–144° C.

Analysis calculated for $C_{23}H_{25}NO_4$ Theory: C, 72.80; H, 6.64; N, 3.69; Found: C, 72.58; H, 6.72; N, 3.77.

As noted above, the compounds of this invention are useful for selectively inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

The term "pharmaceutically effective amount", as used herein, represents an amount of a compound of the invention which is capable of inhibiting serotonin uptake. The particular dose of compound administered according to this invention will, of course, be determined by the particular circumstances surrounding the case, including the specific compound administered, the route of administration, the particular condition being treated, and similar considerations. A typical daily dose will contain from about 0.01 mg/kg to about 20 mg/kg of the active compound of this invention. Preferred daily doses will be about 0.05 mg/kg to about 10 mg/kg, ideally about 0.1 mg/kg to about 5 mg/kg.

The compounds can be administered by a variety of routes including the oral, rectal, transdermal, subcutaneous, intravenous, intramuscular or intranasal routes. It is a special feature of the compounds that they have a prolonged duration of action, and therefore are capable of inhibiting the uptake of serotonin for an extended period of time It is also a special feature of the compounds of the present invention that they have been found to demonstrate a low degree of toxicity to mammals. Finally, it is a special feature of the compounds of the invention that they are extremely selective as inhibitors of serotonin reuptake relative to other monoamine reuptake.

A variety of physiologic functions have been shown to be subject to influence by brain serotoninergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at rates set forth above for inhibiting serotonin uptake in mammals.

The following experiment was conducted to demonstrate the ability of the compounds of the present invention to inhibit the uptake of serotonin. This general procedure is set forth by Wong et al., in *Drug Development Research* 6:397–403 (1985).

Male Sprague-Dawley rats (110–150 g) from Harlan Industries (Cumberland, Ind.) were fed Purina Chow ad libitum for at least 3 days before being used in the studies. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin($^3$H-5-hydroxytryptamine, $^3$H-5HT) was determined as follows. Cortical synaptosomes (equivalent to 1 mg of protein) were incubated at 37° C. for 5 min in 1 ml of Krebsbicarbonate medium containing also 10 mM glucose, 0.1 mM iproniazid, 1 mM ascorbic acid, 0.17 mM EDTA and 50 nM $^3$H-5HT. The reaction mixture was immediately diluted with 2 ml of ice-chilled Krebs-bicarbonate buffer and filtered under vacuum with a cell harvester (Brandel, Gaithersburg, Md). Filters were rinsed twice with approximately 5 ml of ice-chilled 0.9% saline and were transferred to a counting vial containing 10 ml of scintillation fluid (PCS, Amersham, Arlington Heights, Il). Radioactivity was measured by a liquid scintillation spectrophotometer. Accumulation of $^3$H-5HT at 4° C. represented the background and was subtracted from all samples.

The results of the evaluation of various compounds of the present invention are set forth below in Table I. In the Table, column 1 provides the Example Number of the compound evaluated; columns 2–6 identify the structure of the compounds evaluated when taken with the formula set forth in the heading; column 7 identifies the salt form of the compound evaluated; and column 8 provides the concentration of the test compound at $10^{-9}$ M (nM) needed to inhibit 50% of serotonin (5HT), and is indicated in the Table as IC$_{50}$. The numbers in parentheses represent percent inhibition at 1000 nM.

TABLE I
INHIBITION OF 5HT UPTAKE IN VITRO

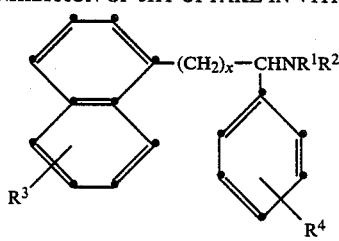

| Compound of Example No. | R$^1$ | R$^2$ | R$^3$ | R$^4$ | x | Salt Form | IC$_{50}$ (nM) 5HT |
|---|---|---|---|---|---|---|---|
| 1 | H | H | H | H | 3 | oxalate | 240 |

TABLE I-continued
INHIBITION OF 5HT UPTAKE IN VITRO

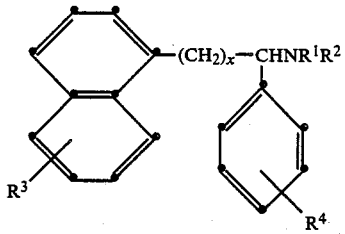

| Compound of Example No. | R$^1$ | R$^2$ | R$^3$ | R$^4$ | x | Salt Form | IC$_{50}$ (nM) 5HT |
|---|---|---|---|---|---|---|---|
| 2 | CH$_3$ | CH$_3$ | H | H | 3 | oxalate | 30 |
| 3 | H | CH$_3$ | H | H | 3 | oxalate | 70 |
| 4 | CH$_3$ | CH$_3$ | H | H | 2 | oxalate | 240 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| (+)-N,N—dimethyl-1-phenyl-4-(1-naphthalenyl)butylaminium tartrate | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| N,N—dimethyl-1-(3-methylphenyl)-3-(1-naphthalenyl)propylaminium oxalate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| N—methyl-1-(4-fluorophenyl)-4-(1-naphthalenyl)butylaminium hydrochloride | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

|  |  |
|---|---|
| (−)-N,N—dimethyl-1-phenyl-5-(1-naphthalenyl)pentylaminium tartrate | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

|  |  |
|---|---|
| N,N—dimethyl-1-phenyl-4-(2-naphthalenyl)butylaminium citrate | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

|  |  |
|---|---|
| 1-(3-chlorophenyl)-4-(1-naphthalenyl)-butylaminium oxalate | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

|  |  |
|---|---|
| N,N—dimethyl-1-phenyl-4-(1-naphthalenyl)butylaminium oxalate | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (−)-N,N—dimethyl-1-phenyl-4-(1-naphthalenyl)butylaminium tartrate | 100 mg |
| isotonic saline | 1000 ml |

The solution of the above ingredients is administered intravenously at a rate of 1 ml per minute to a subject suffering from depression.

We claim:

1. A compound of the formula

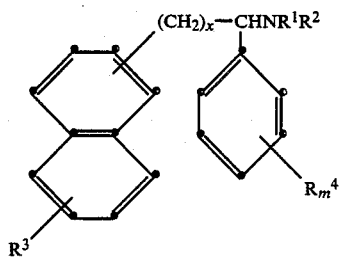

wherein:
each of $R^1$ and $R^2$ independently is hydrogen or methyl;
$R^3$ is hydrogen, halo, $C_1$–$C_4$ alkyl, $C_1$–$C_3$ alkoxy or trifluoromethyl;
each $R^4$ independently is hydrogen, halo, $C_1$–$C_4$ alkyl, $C_1$–$C_3$ alkoxy or trifluoromethyl;
m is 1 or 2;
x is 2–5; or
a pharmaceutically acceptable acid addition salt thereof.

2. A compound of claim 1 wherein both $R^1$ and $R^2$ are hydrogen.

3. The compound of claim 2 which is 1-phenyl-4-(1-naphthalenyl)butylamine, and its pharmaceutically acceptable acid addition salts.

4. The compound of claim 3 which is 1-phenyl-4-(1-naphthalenyl)butyltinium oxalate.

5. A compound of claim 1 wherein one of $R^1$ and $R^2$ is hydrogen and the other is methyl.

6. The compound of claim 5 which is N-methyl-1-phenyl-4-(1-naphthalenyl)butylamine, and its pharmaceutically acceptable acid addition salts.

7. The compound of claim 6 which is N-methyl-1-phenyl-4-(1-naphthalenyl)butylaminium oxalate.

8. The compound of claim 1 wherein both of $R^1$ and $R^2$ are methyl.

9. The compound of claim 8 which is N,N-dimethyl-1-phenyl-3-(1-naphthalenyl)propylamine, and its pharmaceutically acceptable acid addition salts.

10. The compound of claim 9 which is N,N-dimethyl-1-pheyl-3-(1-naphthalenyl)propylaminium oxalate.

11. The compound of claim 8 which is N,N-dimethyl-1-phenyl-4-(1-naphthalenyl)butylamine, and its pharmaceutically acceptable acid addition salts.

12. A compound of claim 11 which is N,N-dimethyl-1-phenyl-4-(1-naphthalenyl)butylaminium oxalate.

13. A method for inhibiting serotonin uptake in mammals which comprises administering to a mammal requiring increased neurotransmission of serotonin a pharmaceutically effective amount of a compound of claim 1.

14. A method of treating depression in humans comprising administering to a human suffering from depression an effective antidepressant dose of a compound of claim 1.

15. A method of treating anxiety in humans comprising administering to a human suffering from anxiety an effective antianxiety dose of a compound of claim 1.

16. A method of treating obesity in humans comprising administering to a human suffering from obesity an effective antiobesity dose of a compound of claim 1.

17. A method of suppressing the desire of humans to smoke comprising administering to a human in need of such suppression an effective dose to relieve the desire to smoke of a compound of claim 1.

18. A method of suppressing the desire of humans to consume alcohol comprising administering to a human in need of such suppression an effective dose to relieve the desire to consume alcohol of a compound of claim 1.

19. A pharmaceutical formulation comprising a compound of claim 1 and a pharmaceutically acceptable carrier, diluent or excipient therefor.

* * * * *